United States Patent [19]
Payard et al.

[11] Patent Number: 5,925,665
[45] Date of Patent: Jul. 20, 1999

[54] IMIDAZOLINE COMPOUNDS

[75] Inventors: Marc Payard, Balma; Saadia Danoun, Toulouse; Geneviève Baziard-Mouysset, Toulouse; Maria Anastassiadou, Toulouse; Daniel-Henri Caignard, Le Pecq; Pierre Renard, Versailles; Dominique Manechez, Puteaux; Elizabeth Scalbert, Boulogne; Marie-Claire Rettori, Courbevoie, all of France

[73] Assignee: Adir Et Compagnie, Courbevoie, France

[21] Appl. No.: 08/984,673

[22] Filed: Dec. 3, 1997

[30] Foreign Application Priority Data

Dec. 4, 1996 [FR] France ...................... 9614844

[51] Int. Cl.[6] ........................ A61K 31/415; C07D 233/64
[52] U.S. Cl. .................. 514/401; 548/347.1; 548/348.1; 548/349.1; 548/351.1; 548/353.1; 548/354.1
[58] Field of Search ............. 548/347.1, 348.1, 548/349.1, 351.1, 353.1, 354.1; 514/401

[56] References Cited

U.S. PATENT DOCUMENTS

| | | | |
|---|---|---|---|
| 4,140,859 | 2/1979 | Houlihan, II | 548/347 |
| 4,298,748 | 11/1991 | Dockner et al. | 548/347 |
| 4,910,206 | 3/1990 | Houlihan, I | 514/292 |
| 5,154,858 | 10/1992 | Wakita et al. | 252/582 |

OTHER PUBLICATIONS

Wagner et al "Agents for Affecting the Rheological, etc" CA 89: 113808 (1978).
Levesque et al, "4,5–Dihydorimidazoles from, etc" CA 96:122690 (1982).
Keem et al, "Dehydrogenation of 2–aryl–2–, etc" CA 72: 121439 (1970).
A. Schulz et al., "Dual action of clonidine on insulin release: suppression, but stimulation when $\alpha_2$–adrenoceptors are blocked", Naunya–Schmiedeberg's Arch Pharmocal (1989) 340: 712–714.
R. E. Klem et al., "Dehydrogenation of 2–Aryl–2–imidazolines with Selenium"Notes XP–002058798, Apr. 1970, p. 403.

*Primary Examiner*—Patricia L. Morris
*Attorney, Agent, or Firm*—Gordon W. Hueschen

[57] ABSTRACT

Compound of formula (I):

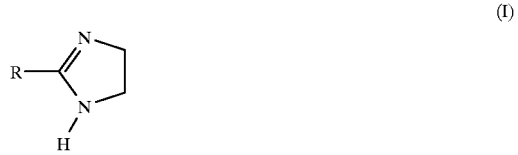

in which R is as defined in the description, as well as their isomers and their pharmaceutically acceptable acid additions salts. Medicinal products containing the same are useful as Imidazoline receptors ligand.

16 Claims, No Drawings

IMIDAZOLINE COMPOUNDS

This present invention relates to new imidazoline compounds, to the process for preparing them and to pharmaceutical compositions containing them.

DESCRIPTION OF THE PRIOR ART

From the point of view of chemical structures, the literature provides many examples of imidazoline derivatives.

For example patents JP-08010871 and EP-501074 claim compounds comprising an imidazoline unit, close to those of the present invention, and which are useful as agents for the cross-linking of epoxy resins.

The studies of E Uhlig et al., (*Z. Anor. Allg. Chem.,* 534, (1986), 188–198) present imidazoline derivatives which act as cupric ion-complexing agents.

When they are used in therapy, the imidazoline derivatives are also very widely described.

For example, patent JP-60209571 presents tetrahydropyrimidines and imidazolines with analgesic properties.

Moreover, many publication (J. N. Sengupta et al., *Naunyn-Schniedeberg's Arch. Pharmacol.,* 335 (4), (1987), 391–396; H. Fuder et al., *Pharmacol. Adrenoreceptors,* (1984), 335–336; R. R. Ruffolo, *Eur. J. Pharmacol.,* 157 (2–3), (1988) 235–239) present pharmacological studies of imidazoline derivatives, ligands of adrenergic receptors.

BACKGROUND OF THE INVENTION

The subject of the present invention is new imidazoline derivatives with an original structure, exhibiting a very high affinity for the imidazoline receptors.

Such derivatives are quite obviously important in the treatment of cardiovascular diseases such as hypertension. Thus, clonidin, widely used for many years in the treatment of high blood pressure is known.

It is known the imidazoline receptors are involved in stimulating the liberation of insulin by the β cells of the pancreas (Schutz et al., *Naunyn-Schniedeberg's Arch. Pharmacol.,* (1989), 340 (6), 712–714).

The importance of ligands of the imidazoline receptors in the treatment of psychiatric and neurological disorders such as depression, Parkinsons's disease and anorexia has also been reported (D. J. Nutt et al., *Annals New York Academy of Science,* (1995), 125–139).

However, most of the imidazoline derivatives known so far have, besides their affinity for the imidazoline receptors, a high affinity for the adrenergic receptors which causes the appearance of strong cardiovascular effects.

The applicant has now discovered new derivatives with an imidazoline structure, potent ligands of the imidazoline receptors but lacking for the adrenergic receptors.

Accordingly, the compounds of the invention find a particularly important use in therapy for the treatment of pathologies linked to the imidazoline receptors by virtue of their high affinity for the receptors, while lacking side effects of central origin, because of their very low affinity for the adrenergic receptors. As a result, the derivatives of the invention are important in the treatment of cardiovascular diseases, of hypertension but also in the treatment of diabetic disease as well as in the treatment of psychiatric and neurological disorders such as depression, Parkinson's disease and anorexia which was not the case for the imidazolines known in the prior art.

DETAILED DESCRIPTION OF THE INVENTION

More specifically, the present invention relates to the compounds of formula (I):

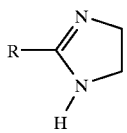

(I)

in which R represents:
either a phenyl radical of formula (α):

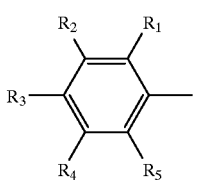

(α)

in which $R_1$ represents:
either a ($C_1$–$C_6$) alkyl radical, and in this case:
either $R_2$ represents a hydrogen atom, as well as $R_3$ and $R_5$, and in this case $R_4$ represents a halogen atom,
or $R_2$ represents a hydrogen atom, as well as $R_4$ and $R_5$, and in this case $R_3$ represents a halogen atom different from chlorine,
or $R_2$ represents a cyano radical, and $R_3$, and $R_4$ and $R_5$, each represent a hydrogen atom,
or a halogen atom, and in this case:
either $R_3$ also represents a halogen atom different from $R_1$, and $R_2$, $R_4$ and $R_5$ each represent a hydrogen atom,
or $R_3$ represents a hydrogen atom as well as $R_2$ and $R_5$, and $R_4$ then represents a ($C_1$–$C_6$) alkyl radical,
or a hydrogen atom, and in this case:
either $R_2$, $R_3$ and $R_4$ represent simultaneously a hydrogen atom and $R_5$ represents a phenyl group,
or $R_2$ and $R_3$ represent simultaneously a halogen atom different from each other, $R_4$ and $R_5$ each a hydrogen atom,
or $R_2$ represents a halogen atom of a ($C_2$–$C_6$) alkyl or ($C_1$–$C_6$) alkylcarbonyl group, and $R_3$, $R_4$ and $R_5$ each represent a hydrogen atom,
or $R_2$ represents a hydrogen atom, as well as $R_4$ and $R_5$ and in this case, $R_3$ is chosen from an ethyl, n-propyl, n-butyl, trifluoromethyl, ($C_1$–$C_6$) alkylthio, trifluoromethoxy, phenyl, phenoxy, ($C_1$–$C_6$) acylamino, aminosulfonyl, aminosulfonyl substituted on the nitrogen atom with one or two ($C_1$–$C_6$) alkyl group),
or $R_2$ represents nitro, $R_3$ represents hydroxy, $R_4$ represents halogen and $R_5$ represents hydrogen,
or $R_3$ $R_5$ each represent hydrogen and $R_2$ and $R_4$ each represent halogen and cannot both represent chlorine,
or a naphthyl radical of formula (β):

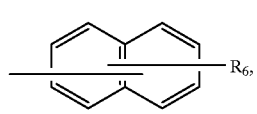

(β)

in which $R_6$ represents a halogen atom, a ($C_1$–$C_6$) alkyl group, or a methoxy group, or a radical chosen from the radicals
indol-5-yl

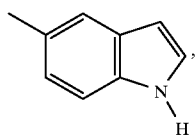

1-phenyl-1-cyclohexylmethyl,
cycloheptyl,
4-(benzothiazol-2-yl)benzyl, and
the radical

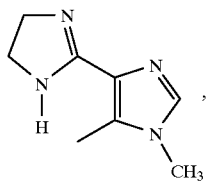

their isomers, as well as their pharmaceutically acceptable acid addition salts, it being understood that, $(C_1-C_6)$ alkyl, $(C_2-C_6)$ alkyl and $(C_1-C_6)$ alkylthio radical are understood to mean both the linear radicals and the branched radicals.

Amount the pharmaceutically acceptable acids which can be used to form and addition salt with the compounds of the invention, there may be mentioned, by way of example and with no limitation being implied, hydrochloric, sulfuric, phosphoric, tartaric, malic, maleic, fumaric, oxalic, methanesulfonic, ethanesulfonic, camphoric and citric acids.

The halogens present in the compounds of general formula (I) are chosen from bromine, chlorine, flourine and iodine.

The invention preferably relates to the compounds of formula:

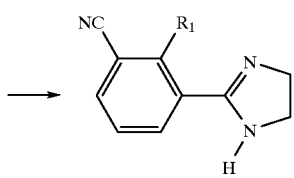

(α I/a)

in which $R_1$ represents linear or branched $(C_1-C_6)$ alkyl group

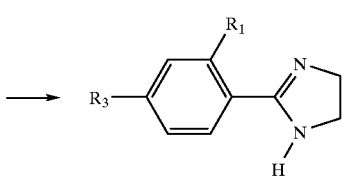

(α I/b)

in which $R_1$ represents a halogen atom or a linear or branched $(C_1-C_6)$ alkyl group, and $R_3$ different from $R_1$ represents a halogen atom,

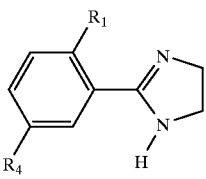

(α I/c)

in which $R_1$ represents a halogen atom and $R_4$ represents a linear or branched $(C_1-C_6)$ alkyl radical,

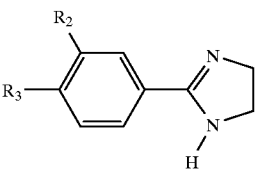

(α I/d)

in which $R_2$ and $R_3$ each represent a halogen atom different from each other,

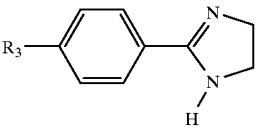

(α I/e)

in which $R_3$ represent a radical chosen from a radical ethyl, n-propyl, n-butyl, trifluoromethyl, $(C_1-C_6)$ alkylthio, trifluoromethoxy, phenyl, phenoxy, $(C_1-C_6)$ acylamino, or amionsulfonyl, aminosulfonyl substituted on the nitrogen atom with one or two linear or branched $(C_1-C_6)$ alkyl groups,

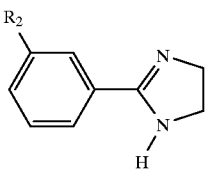

(α I/f)

in which $R_2$ represents a halogen atom or a linear or branched $(C_{2-C_6})$ alkyl group or a linear or branched $(C_1-C_6)$ alkylcarbonyl group.

More particularly, the invention relates to the compounds of formula (I) for which R is chosen from the radicals:

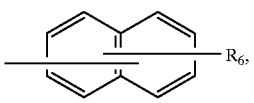

(β)

in which $R_6$ represents a halogen atom, a linear or branched $(C_1-C_6)$ alkyl group, or a methoxy group, for example R represents a 2-methoxy-1-naphthyl group,
5-indolyl,
cycloheptyl.

The invention also relates to the process for the preparation of the compounds of formula (I), wherein a nitrile of formula (II):

$$R-C\equiv N \quad (II)$$

in which R is as defined above, is condensed with ethylenediamine, in the presence of a catalytic quantity of phosphorus pentasulfide, it being possible for the crude compound thus obtained to be, if desired:
- purified according to one or more methods of purification chosen from crystallization, silica gel chromatography, extraction, filtration, passage on charcoal or on resin,
- separated, where appropriate, in a pure form or in the form of a mixture, into its possible isomers, according to conventional separation techniques,
- and/or converted, by an acid, to pharmaceutically acceptable salts.

The raw materials used in the process for the preparation of the compounds of formula (I) are either commercially available or easily available to persons skilled in the art.

The compounds of formula (I) possess very important pharmacological properties for the clinician and the doctor.

The compounds of the invention and the pharmaceutical compositions containing them have proved to be potent ligands of the $I_1$ and/or $I_2$ imidazoline receptors.

The imidazoline receptors are also involved in anemia, particularly sickle cell anemia, and cancerous proliferation.

Moreover, pharmacological studies of the compounds of the invention have demonstrated a complete absence of toxicity in addition to their very high affinity for the imidazoline receptors, which has already been mentioned.

This makes it possible to establish that the compounds of the invention and the pharmaceutical compositions containing them are useful in the treatment of pathologies linked to the central nervous system, and particularly depression, Parkinson's disease, anorexia, cardiovascular pathologies and in particular hypertension, as well as in the treatment of diabetes, obesity, anemia, particularly sickle cell anemia and cancer.

The subject of the present invention is also the pharmaceutical compositions containing the products of formula (I) or, where appropriate, one of their pharmaceutically acceptable acid addition salts in combination with one or more pharmaceutically acceptable excipients.

Among the pharmaceutical compositions according to the invention, there may be mentioned more particularly those which are suitable for oral, parental, nasal, per- or transcutaneous, rectal, perlingual, ocular or respiratory administration and particularly plain or sugar-coated tablets, sublingual tablets, sachets, packets, gelatin capsules, sublingual preparations, lozenges, suppositories, creams, ointments, skin gels, oral or injectable ampoules and aerosols.

The dosage varies according to the sex, age and weight of the patient, the route of administration, the nature of the therapeutic indication, or possible associated treatments and varies between 0.1 mg and 100 mg per 24 hours in 1 or 2 doses, more particularly between 1 and 10 mg, for example between 1 and 2 mg.

The following examples illustrate the invention, but do not limit it in any way.

EXAMPLES 1 TO 30

General procedure:

A mixture consisting of 25 ml of ethylenediamine, 0.01 moles to 0.02 moles of a nitrile and a catalytic quantity (about 0.5 g) of phosphorus pentasulfide is heated under reflux, with stirring, for 4 to 8 hours. The disappearance of the nitrile is followed by thin-layer chromatography. The cooled mixture is poured into 50 ml of cold water. The whole is then extracted with twice 50 ml of dichloromethane. After evaporation of organic fraction, the residue is crystallized from cyclohexane.

By carrying out the procedure as is described in the general and by using the appropriate nitrile, the compounds of the following examples are obtained:

EXAMPLE 1

2-(4-Biphenyl)-$\Delta^2$-imidazoline

Yield: 91%
Melting point: 200° C.

EXAMPLE 2

2-(4-Trifluoromethoxyphenyl)-$\Delta^2$-imidazoline

Yield: 77%
Melting point: 150° C.

EXAMPLE 3

2-(5-Indolyl)-$\Delta^2$-imidazoline

Yield: 60 %
Melting point: 181° C.

EXAMPLE 4

2-(1-Cyclohexyl-1-phenylmethyl)-$\Delta^2$-imidazoline

Yield: 41%
Melting point: 178° C.

EXAMPLE 5

2-[4-(Benzothiazol-2yl)benzyl ]-$\Delta^2$-imidazoline

Yield: 52%
Melting point: 157° C.

EXAMPLE 6

2-(6-Methoxy-2-naphthyl)-$\Delta^2$-imidazoline

Yield: 61%
Melting point: 155° C.

EXAMPLE 7

2-Cycloheptyl-$\Delta^2$-imidazoline

Yield: 77%
Melting point: 255° C.

EXAMPLE 8

2-(4-Ethylphenyl)-$\Delta^2$-imidazoline

Yield: 98%
Melting point: 135° C.

EXAMPLE 9

1-Methyl-4,5-bis($\Delta^2$-imidazoline-2-yl)imidazole

Yield: 84%
Melting point: 162° C.

EXAMPLE 10

2-(4-n-Propylphenyl)-$\Delta^2$-imidazoline

Yield: 70%
Melting point: 126° C.

EXAMPLE 11

2-(4-n-Butylphenyl)-$\Delta^2$-imidazoline

Yield: 61%
Melting point: 98° C.

EXAMPLE 12

2-(3-Cyano-2methylphenyl)-$\Delta^2$-imidazoline

Yield: 78%
Melting point: 144° C.

EXAMPLE 13

2-(4-Phenoxyphenyl)-$\Delta^2$-imidazoline

Yield: 56%
Melting point: 129° C.

EXAMPLE 14

2-(3-Chloro-4-fluorophenyl)-$\Delta^2$-imidazoline

Yield: 41%
Melting point: 109° C.

EXAMPLE 15

2-(2-Chloro-4-fluorophenyl)-$\Delta^2$-imidazoline

Yield: 40%
$^1$H NMR δ (ppm): 2.97 and 3.16 (2m, 4H, 2CH$_2$); 4.93 s, 1H, NH); 6.46 (dd, 1H, J=2.37 and 8.97 Hz, H$_5$); 6.59 (d, 1H, J=2.37 Hz, H$_3$); 7.35 (d, 1H, J=8.71 Hz, H$_6$).

EXAMPLE 16

2-(2-Fluoro-5-methylphenyl)-$\Delta^2$-imidazoline
Yield: 40%
Melting point: 85° C.

EXAMPLE 17

2-(4-Ethylthiophenyl)-$\Delta^2$-imidazoline

EXAMPLE 18

2-(4-Methylthiophenyl)-$\Delta^2$-imidazoline

Yield: 72%
Melting point: 158° C.

EXAMPLE 19

2-(2-Methoxy-1-naphthyl)-$\Delta^2$-imidazoline

Yield: 70%
Melting point: 157° C.

EXAMPLE 20

2-(4-Trifluoromethylphenyl)-$\Delta^2$-imidazoline

Yield: 81%
Melting point: 180° C.

EXAMPLE 21

2-(3-Ethylphenyl)-$\Delta^2$-imidazoline

EXAMPLE 22

2-(2-Phenylphenyl)-$\Delta^2$-imidazoline

EXAMPLE 23

2-(5-Fluoro-2-methylphenyl)-$\Delta^2$-imidazoline

EXAMPLE 24

2-(4-Hydroxy-5-iodo-3-nitrophenyl)-$\Delta^2$-imidazoline

EXAMPLE 25

2-(4-Aminosulfonylphenyl)-$\Delta^2$-imidazoline

EXAMPLE 26

2-(4-Acetylaminophenyl)-$\Delta^2$-imidazoline

EXAMPLE 27

2-(4-Methyl-1-naphthyl)-$\Delta^2$-imidazoline

EXAMPLE 28

2-(4-Fluoro-1naphthyl)-$\Delta^2$-imidazoline

EXAMPLE 29

2-(4-Bromo-2-methylphenyl)-$\Delta^2$-imidazoline

EXAMPLE 30

2-(3,5-Difluorophenyl)-$\Delta^2$-imidazoline

PHARMACOLOGICAL STUDY

EXAMPLE A

Pattern of binding to the $I_1$ and $I_2$ imidazoline receptors

Objective:

To measure, in vitro, the binding affinity of the compounds of the invention to the $I_1$ and $I_2$ receptors, by determining the capacity of these compounds to displace radioligands specific for the $I_1$ and $I_2$ imidazoline receptors.

Protocol:

The following table indicates the radioligand used to label the receptor, the product and the concentration selected to determine the non specific and the tissue chosen.

| Receptor or site | Radioligand | Non specific | Structure |
| --- | --- | --- | --- |
| I$_1$ | [$^3$H]-Clonidine + 10 μM of norepinephrine | 10$^{-5}$M Cold clonidine | Bovine Adrenal Medulla |
| I$_2$ | [$^3$H]-Idazoxan + 10 μM of norepinephrine | 10$^{-5}$M Idazoxan | Rabbit renal cortex |

Results:

The results obtained in vitro on the central or peripheral receptors and with out experimental conditions show that the compounds of the invention have a very high affinity of the I$_1$ and/or I$_2$ sites of rabbit renal cortex with K$_i$ values from a few nM to a few hundreds of nM.

EXAMPLE B

Pattern of binding to the α$_1$ and α$_2$ adrenergic central receptors

Objective:

To measure, in vitro, the binding affinity of the compounds of the invention to the α$_1$ and α$_2$ central receptors, by determining the capacity of the product to displace radioligands specific for these receptors.

Protocol:

The following table indicates the radioligand used to label the receptor, the product and the concentration selected to determine the nonspecific fraction and the tissue chosen.

| Receptor or site | Radioligand | Non specific | Structure |
| --- | --- | --- | --- |
| α$_1$ | [$^3$H]-Prazosin | 10$^{-5}$M Phentolamine | Calf frontal cortex |
| α$_2$ | [$^3$H]-RX 821002 | 10$^{-5}$M Yohimbine | Calf frontal cortex |

Results:

The results obtained, in vitro on the adrenergic receptors with our experimental conditions, show that the compounds of the invention have only a very low affinity for the α$_1$-adrenergic receptors (K$_i$>7 μM) and α$_2$-adrenergic receptors (K$_i$>10 μM).

EXAMPLE C

Test of behavioral despair

The mice used for this test are placed in a cylinder filled with water from which they cannot escape. After a few efforts to get out, the animals become resigned and stay still, now making only the movement necessary to keep the head out of the water. The animals, in groups of ten, are placed in the cylinder for 6 minutes, and the duration of immobility is measured during the last 4 minutes.

The duration of immobility makes it possible to characterize the antidepressive activity of the test compounds. Thus, antidepressants such as imipramine or desipramine decrease this duration of immobility.

The compounds of the invention showed an activity comparable to that of imipramine and desipramine, the duration of immobility measured being of the same order as that obtained with the reference products.

EXAMPLE D

Measurement of affinity for monoamine oxidase

In vitro

The test of binding to the I$_2$ imidazoline site as well as the affinity for monoamine oxidase are carried out according to the protocol described by C. Carpéné (Annals. N.Y. Acad. Sci., 1995, 763, p. 380).

The reference radioligand used is titivated BFI. Competitive binding experiments are carried out with the compounds of the invention with the aim of demonstrating their capacity to displace the reference radioligand.

Ex vivo

The animals used are genetically obese Zücker rats which are subjected to a subchronic treatment with the test compounds. At the end of this test, the binding to the I$_2$ imidazoline sites as well as the monoamine oxidase activity are measured after extraction of the adipose tissue ex vivo according to a method described by C. Carpéné (J. lipids. Res., 1990, 31, p. 811).

Results

It appears that the compounds of the invention possess a high affinity for the I$_2$ imidazoline binding sites, of the order 1 to 100 nM, and an inhibitory effect on monoamine oxidase in the adipocytes by binding to the enzyme with an affinity of the order of 10$^{-6}$M.

EXAMPLE E

Hypoglycemia activity

The hypoglycemia activity of the derivatives of the invention were tested on three-month-old Witsar male rats of about 250 g. An experimental diabetes is obtained by iv injection of a weak dose of streptozotocin dissolved in a citrate buffer (171) under Kétamine hydrochloride anesthesia (75 mg.kg$^{-1}$, IP). These rats are called "STZ", and the normal rats received an injection of citrate buffer under the same conditions.

Homeostasis was evaluated by a test of glucose tolerance carried out two weeks after injection of streptozotocin.

Intravenous glucose tolerance test (IVGTT)

The glucose is dissolved in a 0.9% aqueous NaCl solution and administered through the saphenous vein to rats anesthetized with pentobarbital (60 mg.kg$^{-1}$, IP). Blood samples are collected sequentially through the tail vessels before and 5, 10, 15, 20 and 30 minutes after the injection of glucose. They are then centrifuges and the plasma is separated. The plasma glucose concentration is determined immediately on a 10 μl aliquot and the remaining plasma is stored at −20° C.

A single IP injection of the test product is made into rats anesthetized with pentobarbital, 20 minutes before the IVGTT.

Oral glucose tolerance test (OGTT)

The glucose is administered per os (2 g.kg$^{-1}$) to wakeful rats. Blood samples are collected before and 10, 20, 30, 40, 60, 90 and 120 minutes after the administration of glucose. The treatment of the blood samples is identical to that described above. The test product is administered per os 30 minutes before the OGTT.

Analytical methods

The plasma glucose concentration is determined using a glucose analyzer (Beckman Inc., Fullerton, Calif.). Glucose tolerance is measured in relation to two parameters: ΔG and K. ΔG represents the increase in glycemia above the base line, integrated over a period of 30 minutes (IVGTT) or of 120 minutes (OGTT), after excessive accumulation of glucose. K is the speed of disappearance of glucose between 5 and 30 minutes (IVGTT), after administration of glucose. The coefficient K is calculated only during the IVGTT. It appears that the compounds of the invention have an activity comparable to that of gliclazide, and have the advantage of not inducing the same basal hypoglycemia.

EXAMPLE F

Study of acute toxicity

The acute toxicity was assessed after oral administration to lots of 8 mice (26±2 grams) of increasing doses of the product to be studies. The animals were observed at regular intervals during the first day and daily during the two weeks following the treatment. It appears that the compounds of the invention exhibit very little toxicity.

EXAMPLE G

Pharmaceutical composition: tablets

Preparation formula for 1000 tablets containing 1 mg doses 2-(4-ethylphenyl)-Δ²-imidazoline:

2-(4-Ethylphenyl)-Δ²-imidazoline . . . 1 g
Wheat starch . . . 20 g
Maize starch . . . 20 g
Lactose . . . 30 g
Magnesium stearate . . . 2 g
Silica . . . 1 g
Hydroxypropylcellulose . . . 2 g

We claim:

1. A compound selected from those of formula (I):

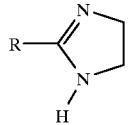

in which R represents:
either a phenyl radical of formula (60 ):

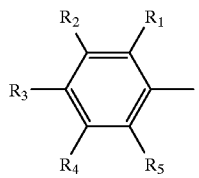

in which $R_1$ represents:
either $(C_1-C_6)$ alkyl, and in this case:
$R_2$ represents cyano, and $R_3$, $R_4$ and $R_5$, each represent hydrogen,
or a halogen atom, and in this case:
either $R_3$ also represents a halogen atom different from $R_1$, and $R_2$, $R_4$ and $R_5$ each represent a hydrogen atom,
or $R_3$ represents a hydrogen atom as well as $R_2$ and $R_5$, and $R_4$ then represents a $(C_1-C_6)$ alkyl radical,
or hydrogen, and in this case:
either $R_2$, $R_3$ and $R_4$ represent simultaneously hydrogen and $R_5$ represents phenyl,
or $R_2$ and $R_3$ different from each other represent simultaneously halogen, and $R_4$ and $R_5$ each represent hydrogen, or $R_2$ represents $(C_2-C_6)$ alkyl or $(C_1-C_6)$ alkylcarbonyl, and $R_3$, $R_4$ and $R_5$ each represent hydrogen,
or $R_2$ represents hydrogen, as well as $R_4$ and $R_5$, and in this case, $R_3$ is chosen from ethyl, n-propyl, n-butyl, trifluoromethyl, $(C_1-C_6)$ alkylthio, trifluoromethoxy, phenyl, phenoxy, $(C_1-C_6)$ acylamino, aminosulfonyl, aminosulfonyl substituted on the nitrogen atom with one or two $(C_1-C_6$ alkyl),
or $R_2$ represents nitro, $R_3$ represents hydroxy, $R_4$ represents halogen, and $R_5$ represents hydrogen,
or $R_3$ and $R_5$ each represent hydrogen and $R_2$ and $R_4$ each represent halogen and cannot both represent chlorine, or a naphthyl radical of formula (β):

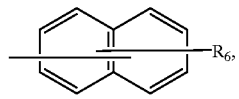

in which $R_6$ represents halogen, $(C_1-C_6)$ alkyl, or methoxy,
or a radical chosen from the radicals
1-cyclohexyl-1-phenylmethyl, and
cycloheptyl,
their optical isomers, or their pharmaceutically acceptable-acid addition salt,
it being understood that, $(C_1-C_6)$ alkyl, $(C_2-C_6)$ alkyl, and $C_1-C_6$ alkylthio are understood to mean both linear and branched radicals.

2. A compound of claim 1 of formula (αI/a):

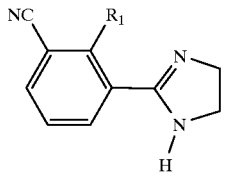

in which $R_1$ represents linear or branched $(C_1-C_6)$ alkyl, their optical isomers, or their pharmaceutically acceptable acid addition salts.

3. A compound of claim 1 of formula (αI/a):

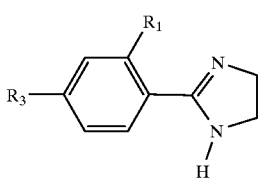

in which $R_1$ represents halogen and $R_3$ different from $R_1$ represents halogen, their optical isomers or their pharmaceutically-acceptable acid addition salts.

4. A compound of claim 1 of formula (αI/c):

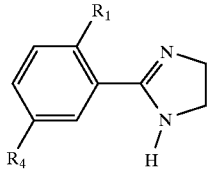
(α I/c)

in which $R_1$ represents halogen and $R_4$ represent linear or branched ($C_1$–$C_6$) alkyl, their optical isomers, or their pharmaceutically-acceptable acid addition salts.

5. A compound of claim 1 of formula (αI/d):

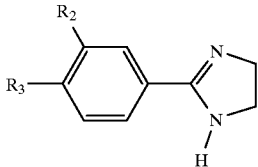
(α I/d)

in which $R_2$ and $R_3$ represent halogen different from each other, their opticals isomers or their pharmaceutically-acceptable acid addition salts.

6. A compound of claim 1 of formula (αI/e):

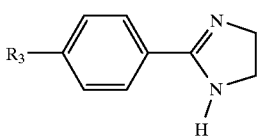
(α I/e)

in which $R_3$ represents a radical chosen from ethyl, n-propyl, n-butyl, trifluoromethyl, ($C_1$–$C_6$) alkylthio, trifluoromethoxy, phenyl, phenoxy, ($C_1$–$C_6$) acylamino, or amionsulfonyl, aminosulfonyl substituted on the nitrogen atom with one or two linear or branched ($C_1$–$C_6$) alkyl, their optical isomers or their pharmaceutically-acceptable acid addition salts.

7. A compound of claim 1 of formula (αI/f):

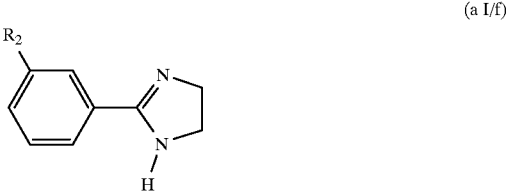
(a I/f)

in which $R_2$ represents linear or branched ($C_2$–$C_6$) alkyl or linear or branched ($C_1$–$C_6$) alkylcarbonyl, their optical isomers or their pharmaceutically-acceptable acid addition salts.

8. A compound of claim 1 for which R represents a radical β

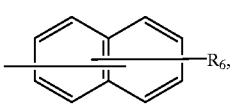
(β)

in which $R_6$ represents halogen, linear or branched ($C_1$–$C_6$) alkyl, or methoxy, their optical isomers, or their pharmaceutically-acceptable acid addition salts.

9. A compound of claim 1 which is selected from 2-(4-biphenyl)-$\Delta^2$-imidazoline or addition salts thereof with a pharmaceutically-acceptable acid.

10. A compound of claim 1 which is selected from 2-(3-cyano-1-methylphenyl)-$\Delta^2$-imidazoline or addition salts thereof with a pharmaceutically-acceptable acid.

11. A compound of claim 1 which is selected form 2-(4-phenoxyphenyl)-$\Delta^2$-imidazoline or addition salts thereof with a pharmaceutically-acceptable acid.

12. A compound of claim 1 which is selected from 2-(4-ethylphenyl)-$\Delta^2$-imidazoline or addition salts thereof with a pharmaceutically-acceptable acid.

13. A pharmaceutical composition useful as a ligand of imidazoline receptors comprising as active principle an effective amount of a compound as claimed in claim 1, together with one or more pharmaceutically-acceptable excipients or vehicles.

14. A method for treating a living body afflicted with a diabetic condition comprising the step of administering to the living body an amount of a compound of claim 1 which is effective for alleviation of the said condition.

15. A compound of claim 1 in which is selected from 2-(1-Cyclohexyl-1-phenylmethyl)-$\Delta^2$-imidazoline or pharmaceutically-acceptable acid addition salts thereof.

16. A compound of claim 1 which is selected from 2-Cycloheptyl-$\Delta^2$-imidazoline or pharmaceutically-acceptable acid addition salts thereof.

* * * * *

UNITED STATES PATENT AND TRADEMARK OFFICE
CERTIFICATE OF CORRECTION

PATENT NO. : 5,925,665                     Page 1 of 5
DATED : Jul. 20, 1999
INVENTOR(S) : M. Payard, S. Danoun, G. Baziard-Mouysset, M. Anastassiadou, D.-H. Caignard, P. Renard, D. Manechez, E. Scalbert, M.-C. Rettori It is certified that error appears in the above-identified patent and that said Letters Patent is hereby corrected as shown below:

Title Page, Column 2, OTHER PUBLICATIONS, line 3:
"4,5-Dihydorimidazoles" should read -- 4,5-Dihydroimidazoles --.

Column 1, line 9: JP-08010871" should read -- JP-07010871 --.

Column 1, line 20: Insert an -- s -- at the end of the word "publication".

Column 1, line 35: Insert -- also -- between "is" and "known".

Column 2, line 28: Delete the second instance "and".

Column 2, line 42: "of a" should read -- or a --.

Column 2, line 54: Insert the word -- and -- between "$R_3$" and "$R_5$".

Column 3, line 31: The word "and" should read -- an --.

Column 4, line 34: Insert an -- s -- at the end of the word "represent".

Column 4, line 37: "amionsulfonyl" should read -- aminosulfonyl --.

Column 4, line 51: "$(C_2-c_6)$" should read -- $(C_2-C_6)$ --.

UNITED STATES PATENT AND TRADEMARK OFFICE
CERTIFICATE OF CORRECTION

PATENT NO. : 5,925,665  
DATED : Jul. 20, 1999  
INVENTOR(S) : M. Payard, S. Danoun, G. Baziard-Mouysset, M. Anastassiadou, D.-H. Caignard, P. Renard, D. Manechez, E. Scalbert, M.-C. Rettori Page 2 of 5

It is certified that error appears in the above-identified patent and that said Letters Patent is hereby corrected as shown below:

Column 6, line 13: Insert the word -- procedure --, after "general".

Column 7, line 48: Insert -- ( -- before the "s," at the end of the line.

Column 7, line 49: "8.97" should read --8.71 --.

Column 8, line 44 (approx): "2-(4-Fluoro-1naphthyl)-" should read -- 2-(4-Fluoro-1-naphthyl)- --.

Column 8, line 67: Insert -- fraction -- after the word "specific".

Column 10, line 5: "The test of" at the beginning of the line, should read -- The tests of --.

Column 10, line 9: "titivated" should read -- tritiated --.

Column 10, line 29: "Hypoglycemia" should read -- Hypoglycemic --.

Column 10, line 31: "hypoglycemia" should read -- hypoglycemic --.

Column 10, line 47: "centrifuges" should read -- centrifuged --.

Column 11, line 12: "studies" should read -- studied --.

Column 11, line 20: After the word "doses", insert -- of --.

Column 11, line 41: "(60):" at the end of the line, should read -- ($\alpha$): --.

UNITED STATES PATENT AND TRADEMARK OFFICE
CERTIFICATE OF CORRECTION

PATENT NO. : 5,925,665
DATED : Jul. 20, 1999
INVENTOR(S) : M. Payard, S. Danoun, G. Baziard-Mouysset, M. Anastassiadou, D.-H. Caignard, P. Renard, D. Manechez, E. Scalbert, M.-C. Rettori It is certified that error appears in the above-identified patent and that said Letters Patent is hereby corrected as shown below:

Column 12, line 12: "$(C_1-C_6 alkyl)$," should read -- $(C_1-C_6)alkyl$, --

Column 12, line 32(approx): Insert the word -- or -- at the beginning of the line.

Column 12, line 33: Insert a -- - -- (hyphen) at the end of "pharmaceutically".

Column 12, line 34: Delete the "-" after "acceptable"; and "addition salt," should read -- addition salts, --

Column 12, line 35: Delete the "comma" after the word "that".

Column 12, line 51: Insert the word -- or -- at the beginning of the line.

Column 12, line 51: Insert a -- - -- (hyphen) between the word "pharmaceutically" and "accept-".

Column 12, line 53: At the end of the line, "($\alpha I/a$):" should read -- ($\alpha I/b$): --.

Column 12, line 66: Insert -- or -- before the word "their".

Column 13, line 14: Insert an -- s -- after the word "represent".

Column 13, line 15: Insert "or" before the word "their".

UNITED STATES PATENT AND TRADEMARK OFFICE
CERTIFICATE OF CORRECTION

PATENT NO.   : 5,925,665
DATED        : Jul. 20, 1999
INVENTOR(S)  : M. Payard, S. Danoun, G. Baziard-Mouysset,
               M. Anastassiadou, D.-H. Caignard, P. Renard,
               D. Manechez, E. Scalbert, M.-C. Rettori Page 4 of 5

It is certified that error appears in the above-identified patent and that said Letters Patent is hereby corrected as shown below:

Column 13, line 31:   After "R$_3$" insert the word -- each --.

Column 13, line 32:   Insert -- or -- before the word "their".

Column 13, line 32:   "opticals" should read -- optical --.

Column 13, line 32:   Insert a -- , -- (comma) after the word "isomers".

Column 13, line 49:   "amionsulfonyl," should read -- aminosulfonyl, --.

Column 13, line 51:   Insert -- or -- before the word "their".

Column 13, line 51:   Insert a -- , -- (comma) after the word "isomers".

Column 14, line 12(approx):   Insert the word -- or -- before "their".

Column 14, line 13(approx):   Insert a -- , -- (comma) after the word "isomers".

UNITED STATES PATENT AND TRADEMARK OFFICE
CERTIFICATE OF CORRECTION

PATENT NO. : 5,925,665
DATED : Jul. 20, 1999
INVENTOR(S) : M. Payard, S. Danoun, G. Baziard-Mouysset, M. Anastassiadou, D.-H. Caignard, P. Renard, D. Manechez, E. Scalbert, M.-C. Rettori It is certified that error appears in the above-identified patent and that said Letters Patent is hereby corrected as shown below:

Column 14, line 26: Insert the word -- or -- before "their".

Column 14, line 32 (approx): "2-(3-cyano-1-" should read -- 2-(3-cyano-2- --.

Column 14, line 34: "form" at the end of the line should read -- from --.

Column 14, line 47: Delete the word "in". Response to Restriction

Signed and Sealed this

Tenth Day of October, 2000

Attest:

Q. TODD DICKINSON

*Attesting Officer*     *Director of Patents and Trademarks*